(12) United States Patent
Strader et al.

(10) Patent No.: US 11,442,614 B2
(45) Date of Patent: *Sep. 13, 2022

(54) METHOD AND SYSTEM FOR GENERATING TRANSCRIPTS OF PATIENT-HEALTHCARE PROVIDER CONVERSATIONS

(71) Applicant: Google LLC, Mountain View, CA (US)

(72) Inventors: Melissa Strader, San Jose, CA (US); William Ito, Mountain View, CA (US); Christopher Co, Saratoga, CA (US); Katherine Chou, Palo Alto, CA (US); Alvin Rajkomar, Mountain View, CA (US); Rebecca Rolfe, Menlo Park, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/215,512

(22) Filed: Mar. 29, 2021

(65) Prior Publication Data

US 2021/0216200 A1 Jul. 15, 2021

Related U.S. Application Data

(63) Continuation of application No. 16/909,115, filed on Jun. 23, 2020, now Pat. No. 10,990,266, which is a (Continued)

(51) Int. Cl.
*G06F 3/04855* (2022.01)
*G16H 10/20* (2018.01)
(Continued)

(52) U.S. Cl.
CPC ........ *G06F 3/04855* (2013.01); *G06F 40/289* (2020.01); *G06F 40/30* (2020.01); *G10L 15/26* (2013.01); *G16H 10/20* (2018.01)

(58) Field of Classification Search
CPC ......... G11B 27/34; G06F 17/24; H04L 51/12; H04L 12/1827; G16H 50/30; A61B 5/0022; A61B 5/4821; G06Q 10/10
See application file for complete search history.

(56) References Cited

U.S. PATENT DOCUMENTS 8,972,269 B2 3/2015 Hoeg
2010/0121637 A1* 5/2010 Roy .................. G10L 15/22
704/235

(Continued)

*Primary Examiner* — Toan H Vu
(74) *Attorney, Agent, or Firm* — McDonnell Boehnen Hulbert & Berghoff LLP

(57) ABSTRACT

A method and workstation for generating a transcript of a conversation between a patient and a healthcare practitioner is disclosed. A workstation is provided with a tool for rendering of an audio recording of the conversation and generating a display of a transcript of the audio recording using a speech-to-text engine, thereby enabling inspection of the accuracy of conversion of speech to text. A tool is provided for scrolling through the transcript and rendering the portion of the audio according to the position of the scrolling. There is a highlighting in the transcript of words or phrases spoken by the patient relating to symptoms, medications or other medically relevant concepts. Additionally, there is provided a set of transcript supplement tools enabling editing of specific portions of the transcript based on the content of the corresponding portion of audio recording.

20 Claims, 10 Drawing Sheets

Related U.S. Application Data continuation of application No. 15/988,657, filed on May 24, 2018, now Pat. No. 10,719,222.

(60) Provisional application No. 62/575,725, filed on Oct. 23, 2017.

(51) Int. Cl.
*G10L 15/26* (2006.01)
*G06F 40/30* (2020.01)
*G06F 40/289* (2020.01)

(56) References Cited

U.S. PATENT DOCUMENTS

| | | | |
|---|---|---|---|
| 2012/0033948 A1* | 2/2012 | Rodriguez | G11B 27/34 386/282 |
| 2012/0232422 A1 | 9/2012 | Donofrio et al. | |
| 2013/0246098 A1* | 9/2013 | Habboush | G06Q 10/087 705/3 |
| 2013/0298016 A1* | 11/2013 | Chigier | G06F 40/103 715/256 |
| 2014/0337989 A1* | 11/2014 | Orsini | G06F 40/51 726/26 |
| 2015/0149540 A1 | 5/2015 | Barker et al. | |
| 2015/0216413 A1 | 8/2015 | Soyao et al. | |
| 2017/0125014 A1 | 5/2017 | Pogorelik et al. | |
| 2017/0364741 A1* | 12/2017 | Hau | G06K 9/72 |
| 2017/0365183 A1* | 12/2017 | Frieder | G09B 7/00 |
| 2018/0165062 A1* | 6/2018 | Yoo | G16H 40/20 |
| 2018/0365385 A1* | 12/2018 | Cooney | G16H 20/17 |

* cited by examiner

Symptoms
"feeling... feverish"
  onset: yesterday afternoon
  tempo: felt worse this morning 1702 → "rash"
1704 → location: right shin Vitals
Temp: 98
Pulse: 84
BP: 110/84
Wt: 176kg
BMI: 25.8

Chief complaint
"leg hurts"

HPI
"feeling feverish"
  onset: "yesterday afternoon"
  alleviating: "tried to sleep it off"
  tempo: "felt worse this morning"

5     Anything?
6  PT  No, everything is the same.
7  DR  AI  Amlodipine | Lipozone | X
1902 → 8  PT  I am. Lipodrene?
9  CG  Yes. How's it going?

Roboto • 11 • B *I* U A

METHOD AND SYSTEM FOR GENERATING TRANSCRIPTS OF PATIENT-HEALTHCARE PROVIDER CONVERSATIONS

PRIORITY

This application is a continuation of U.S. Ser. No. 16/909,115 filed Jun. 23, 2020, and published as U.S. Patent Publication No. 2020/031,9787, which is a continuation of U.S. Ser. No. 15/988,657 filed May 24, 2018, and issued as U.S. Pat. No. 10,719,222 on Jul. 21, 2020, and claims priority to U.S. Provisional Application Ser. No. 62/575,725 filed Oct. 23, 2017, the contents of which are incorporated by reference herein.

BACKGROUND

This disclosure relates generally to the field of medical documentation and note generation, that is, the process by which a healthcare provider (physician or nurse) makes a record of pertinent medical information gained as a result of a visit with a patient. Currently, physicians spend an average of 20 percent of their time (2-3 hours per day) documenting patient visits by creating notes (i.e., text descriptions of symptoms, chief complaint, relevant medical history, and other pertinent information gained during the visit) in the patient's electronic health record. The notes also facilitate proper billing of the patient or their insurance company.

There exists a need in the art for methods and systems improving the efficiency of generating notes of patient visits that takes less time of physicians, allowing them to see more patients and spend more time on patient care. There also exists an unmet need for providing transparency into the machine transcription and information extraction processes to build trust and credibility into the transcription and note generation processes, while also minimizing the impact on the user's attention. This disclosure meets these needs. Additionally, this disclosure can be said to refer to novel interfaces and interactions on a workstation that provide supportive emphasis and rapid understanding of machine intelligence outputs in the context of medical documentation.

SUMMARY

This disclosure relates to an interface (e.g., a display of a workstation used by a provider) for displaying a transcript of a patient-healthcare provider conversation and automated generation of a note or summary of the conversation using machine learning. The transcript and note can be generated in substantial real time during the office visit when the conversation is occurring, or later after the visit is over.

The method includes a step of providing on a workstation a tool for rendering an audio recording of the conversation. The method further includes a step of displaying on a display of the workstation (1) in first transcript region a transcript of the recording in substantial real time with the rendering of the audio recording and simultaneously (2) in a second note region a note summarizing the conversation, the note including automatically extracted words or phrases in the transcript related to medical topics relating to the patient, the extraction of the words or phrase performed with the aid of a trained machine learning model. The medical topics relating to the patient could be such things as symptoms and attributes thereof such as onset, tempo, severity, location, etc., medications, complaints, etc. The method further includes a step of providing links or a mapping between the extracted words or phrases in the note and the portions of the transcript from which the extracted words or phrases originated whereby the source and accuracy of the extracted words or phrases in the note can be verified by a user, for example by selecting one of the extracted words or phrases in the note or by inspection of the note side by side with the transcript with the extracted words or phrases highlighted in both the transcript and the note.

The disclosure also features many different aspects and variations of the above method. For example, the speakers are identified, i.e., patient and physician. At the same time as the written transcript is generated, medically relevant words or phrases in the transcript are extracted from the conversation and automatically populated into a note displayed on the same screen as the transcript. The extracted words or phrases in the note are linked to the corresponding portions of the transcript from which they originated. The physician can thus inspect the transcript and the extraction of relevant words and phrases and the auto-generation of the note to confirm the accuracy of the note. The words or phrase can be placed into appropriate categories or classifications in the note such as under headings for symptoms, medications, etc. The transcript (and note) are editable, with version control to approve, reject or provide feedback on generated suggestions for editing the transcript. Alternative words are suggested for speech in the transcript that does not match vocabulary in the automated speech recognition, or for muffled and partially audible voice input.

The disclosure also relates to aspects of the auto-generated note itself, including among other things expansion of the note to prose in key sections or bullet lists of terms based on the doctor's preference; symptom entities and symptom attributes are grouped by classifiers and placed into specific buckets in the notes. The note is editable to move classifiers and groupings or to add new content. There is a feature for display of confidence level for generated suggestions when certain doubt levels are present, e.g., when the speech is muffled, the patient mispronounces a word, or does not completely remember the name of the medication they are taking. Additionally, the interface can include a display of suggestions during the visit or as reminders to follow-up with the patient, such as suggested questions to ask or suggested billing codes with portions of the transcript displayed which justify the billing codes. Additionally there is a feature for providing an emailable or SMS-ready list of patient instructions at the end of visit, including features for editing the list of instructions, adding new instructions from a list of available or suggested instructions, and a feature to note medication changes or additions in a list generated from the assessment and plan portion of the doctor's notes.

Additionally, this disclosure further describes a method for generating a transcript of an audio recording of a patient-healthcare provider conversation. The disclosure is related to methods to increase the trust and credibility in the transcript.

The method uses a workstation which provides for a rendering of an audio recording of the conversation (e.g., through a speaker on the workstation) and generating a display of a transcript of the audio recording using a speech-to-text engine in substantial real time with the rendering of the audio recording. The generating of the transcript in substantial real time with the rendering of the audio recording enables inspection of the transcript and verification of the accuracy of conversion of speech to text, thereby increasing the confidence that the transcript is accurate. The workstation includes a tool such as a scroll bar for scrolling through full length of the transcript and rendering the portion of the audio according to the position of the scrolling through the transcript. Thus, the user can navigate through the transcript and re-play the portion of the audio at particular points in the transcript to confirm the accuracy of the conversion of speech to text.

Additionally, the method involves highlighting in the transcript words or phrases spoken by the patient relating to symptoms, medications or other medically relevant concepts. For example if the patient says "I felt feverish this morning" the phrase "felt feverish" or just "feverish" and the phrase "this morning" would be highlighted in the transcript, as they are relating to symptoms and onset of symptoms experienced by the patient. This feature calls out to the user's attention particularly important or significant words or phrases in the transcript.

Additionally, the method provides a set of transcript supplement tools which enable editing of specific portions of the transcript based on the content of the corresponding portion of audio recording. In particular, there may be portions of the audio recording where the patient's voice may be muffled, they may mispronounce a significant word, such as the name of a medication, they only remember the first syllable or the pill color of the medication they are taking, etc. The transcription supplement tools enable editing of these portions of the transcript, such as by displaying suggested alternative phrases, displaying corrected medical terminology, displaying suggestions for incomplete words, etc., and tools for accepting, rejecting or editing the transcript and the generated suggestions.

BRIEF DESCRIPTION OF THE DRAWINGS

FIG. 1 also illustrates several aspects of the machine learning system.

FIG. 17 is an illustration of the bullet form of a note like FIG. 6, but augmented with a new symptom "rash" and location: right shin when the patient tells their physician "I also have developed a rash on my right shin . . . " immediately after describing their fever symptoms.

FIG. 18 is another example of a portion of a note automatically generated from an audio recording in a bulleted list format.

FIG. 19 is an illustration of automatically generated suggestions for the term spoken by the patient "Lipodrene"; the physician has the ability to accept or reject the suggestions.

DETAILED DESCRIPTION

Overview

Figure 1:
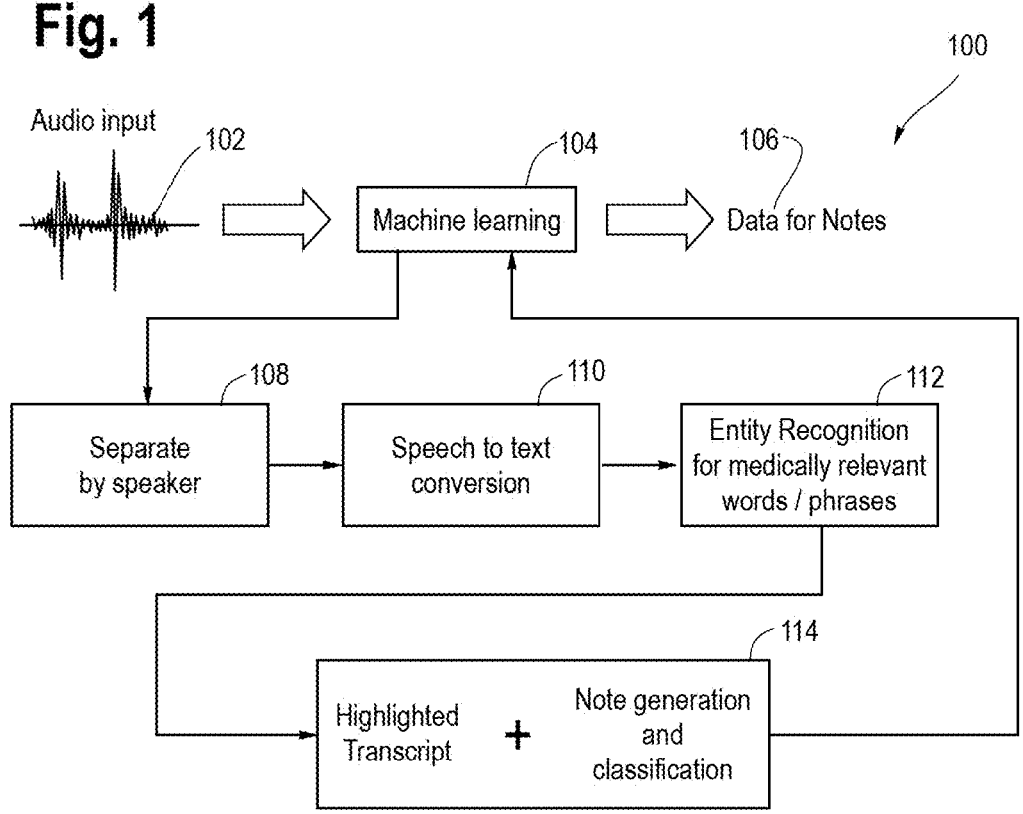
FIG. 1 is an illustration of the flow of data from audio input of a patient-healthcare provider visit into a machine learning system and generating an output in the form of a set of data for a note of a patient visit and a transcript.

One aspect of the present disclosure relates to automated generation of a transcript of a patient-healthcare provider conversation and a physician's note documenting the conversation. The flow of information and software processing is shown in FIG. 1 by the reference number 100. There is an audio input 102 which is made by a recording device present in the room where the conversation takes place. The recording device could, for example, consist of the microphone function of a physician's workstation (210, FIG. 2) and conventional audio recording software present in the workstation. Alternatively, the recording device could consist of a special purpose audio recording unit consisting of microphones and software built into or part of the physician's office. The audio input 102 is provided to a machine learning model 104 (or system in the form of a collection of machine learning models) which generates a transcript of the recording and extracts words or phrases in the transcript which form data 106 for a note. The machine learning model 104 is shown in FIG. 1 as composed of discrete models implemented in software and hardware, including a model 108 which separates the audio input into speech by different speakers, in this case the patient and the healthcare provider. This model 108 can be trained by both the patient and the healthcare provider providing speech training examples. Once the audio input has been separated by speaker by model 108, the audio input is provided to a speech to text conversion model 110. This model implements traditional speech to text functionality but the model 110 is trained using supervised learning techniques and labeled training speech data to recognize medical-related terminology in speech, including things such as symptoms, medications, human anatomical terms, etc.

A named entity recognition model 112 is further included which processes the text generated by the speech to text conversion model 110 to recognize medically relevant words or phrases. Named entity recognition (NER) models are well known in the field of machine learning and are described extensively in the scientific literature. The NER model 112 needs its owned labelled training data. For this training data we use a large corpus of medical text books (over 120,000 medical text books) using deep learning word embedding, in conjunction with a large lexicon of existing medical ontologies, e.g., UMLS (unified medical language system) and SNOMED (systemized nomenclature of medicine). Additionally, the NER model 112 can be trained from annotated medical encounter transcripts. A NER model can also be trained from a hybrid of data sources, which may include medical and clinical text books, annotated transcripts from doctor-patient conversations, and clinical documentation contained in anonymized electronic health records of a multitude of patients.

The result of the application of the named entity recognition model 112 as applied to the text generated by the speech to text conversion model 110 is a highlighted transcript of the audio input 102 with relevant words or phrases highlighted (as recognized by the named entity recognition model) as well as extraction of such highlighted words or text as data for note generation and classification of highlighted words or phrases into different regions or fields of a note as indicated at 114. The application of these models to an audio file and generation of a transcript and note will be explained in detail in subsequent sections of this document.

Figure 2:
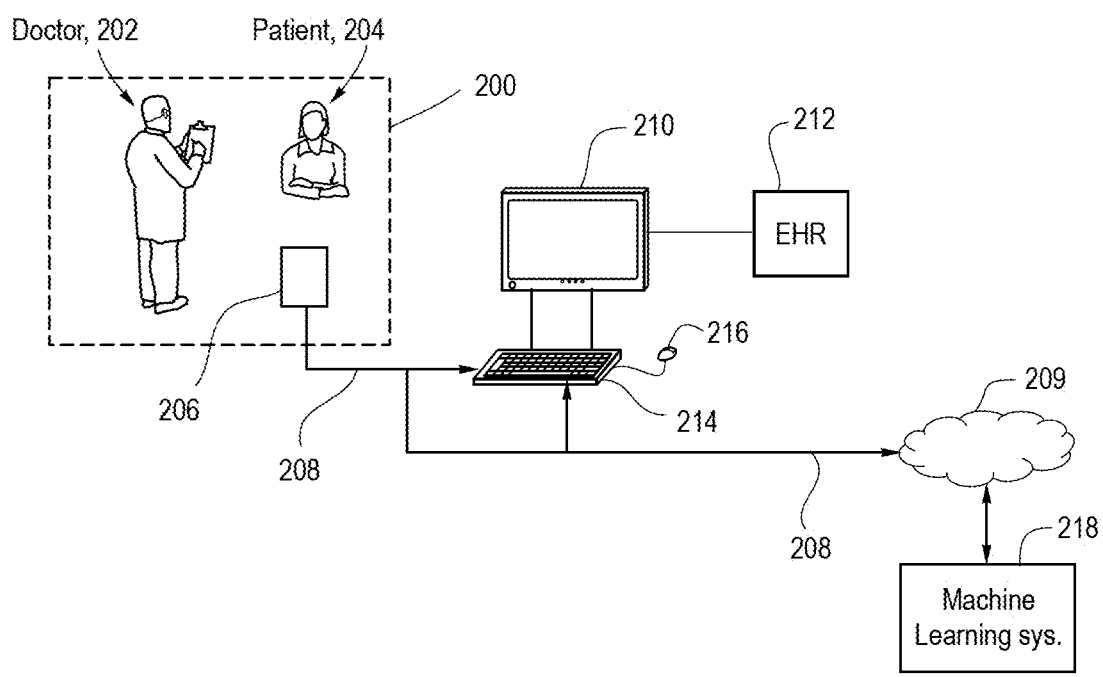
FIG. 2 is block diagram of a computing environment in which the features of the present disclosure can be practiced.

FIG. 2 is an illustration of one possible physical configuration of a computing environment in which the features of this disclosure can be implemented. A clinic, hospital or medical office 200 is the location of visit between a healthcare provider 202 and a patient 204. At that location 200 is a recording device 206 (which may be physically connected to or part of the workstation 210) for capturing and recording the speech of both the provider 202 and the patient 204. This recording is converted to digital form and optionally provided over a computer network 208 to a workstation 210 which is used by the provider 202 to view the transcript and the note generated in accordance with the features of this disclosure. In one format, the workstation (which may be present at the location, e.g., in the physician's office during the visit with the patient) may take the form of a desktop computer which includes an interface in the form of a display, a keyboard 214 and a mouse 216, as well as microphone built in to record the conversation. The workstation 210 could also take the form of a tablet computer, laptop, smart phone or other format, which includes a facility to render (play) the audio recording, display the transcript, and display the note, and include the tools explained below for editing the transcript and note. The workstation 210 also has access to the patient's electronic health record (EHR) either by having it stored locally in data store 212 or accessible via a network connection.

In FIG. 2, the audio input is also sent over a network 208 and cloud 209 to an entity, such as a service provider, which includes a machine learning system 218 implementing the machine learning models 104 of FIG. 1. The entity or service provider implementing the machine learning models generates the transcript and note and transmits them over an application programming interface to software resident on the workstation 210 to render the transcript and note in substantial real time as the audio is being recorded (or later on, when recording is played on the workstation). Further details on the design and implementation of the system of FIG. 2 are not particularly relevant to the present discussion and are omitted for the sake of brevity and in order to not obfuscate the salient details of the present disclosure. The illustrations, screen display, or pages shown in the subsequent Figures are rendered on the display of the workstation 210.

In one possible configuration the workstation 210 could function as a stand-alone system for generating the transcript and the note, in which case the machine learning aspects of FIG. 1 are built into special purpose processors and computing apparatus on the workstation. This embodiment would be suitable for use in remote areas where internet access is not available or unreliable.

Alternatively, the machine learning system 218 of FIG. 2 could be implemented in a local facility to the office 200, such as in a general purpose computer or set of computers on the local area network 208. Or, as shown in FIG. 2, the machine learning system 218 could reside in the could 209 in which case the system receives the audio signal of the doctor-patient conversation and generates the transcript and note data and sends it back to the workstation 210 for display on the workstation's display.

A. Automated Generation of Notes of Patient-Healthcare Provider Conversations

The readers' attention will now be directed to FIGS. 3-14. We will now describe a method for generating a note summarizing a conversation between a patient and a healthcare provider. As will be explained in greater detail below in conjunction with FIG. 3, in essence we provide on a workstation (210 of FIG. 2) a tool (e.g., icon, tab, link, or other action on the interface) for rendering, i.e., playing on speaker associated with the workstation, an audio recording of the conversation and generating a transcript of the audio recording using a speech-to-text engine (part of the model 110 of FIG. 1). We then display on a first region 312 (FIG. 3) of a display of the workstation the transcript of the recording and simultaneously on a second region 314 of the display a note summarizing the conversation. Additionally, the method includes a step of extracting words or phrases in the transcript related to medical topics relating to the health condition of the patient (such as symptoms, medications, chief complaint, relevant medical history, etc.) with the aid of a trained machine learning model (NER model 112 of FIG. 1) and displaying in the second region 314 of the workstation the extracted words or phrase. For example, if the patient speaks the words "I felt feverish" the term "feverish" is highlighted in the transcript region 312 and the term "fever" or "feeling feverish" is shown in the note region 314, e.g., under a symptom heading or as part of a prose sentence such as "The patient complained of feeling feverish."

Furthermore, in the method links or mapping is provided between the extracted/highlighted words or phrases in the note region 314 and the portions of the transcript from which the extracted words or phrases originated whereby the source and accuracy of the extracted words or phrases can be verified by a user of the workstation. For example, if the user of the workstation clicked on the extracted phrase "feeling feverish" in the note region 314, the transcript region 312 will show the portion of the transcript in which the patient said they were feeling feverish. Similarly, if the user clicked on the highlighted term "feeling feverish" in the transcript region the corresponding note element "feeling feverish" or "fever" is shown in the note under a symptom heading, or the sentence "The patient complained of feeling feverish." is shown with "feeling feverish" highlighted.

Figure 3:
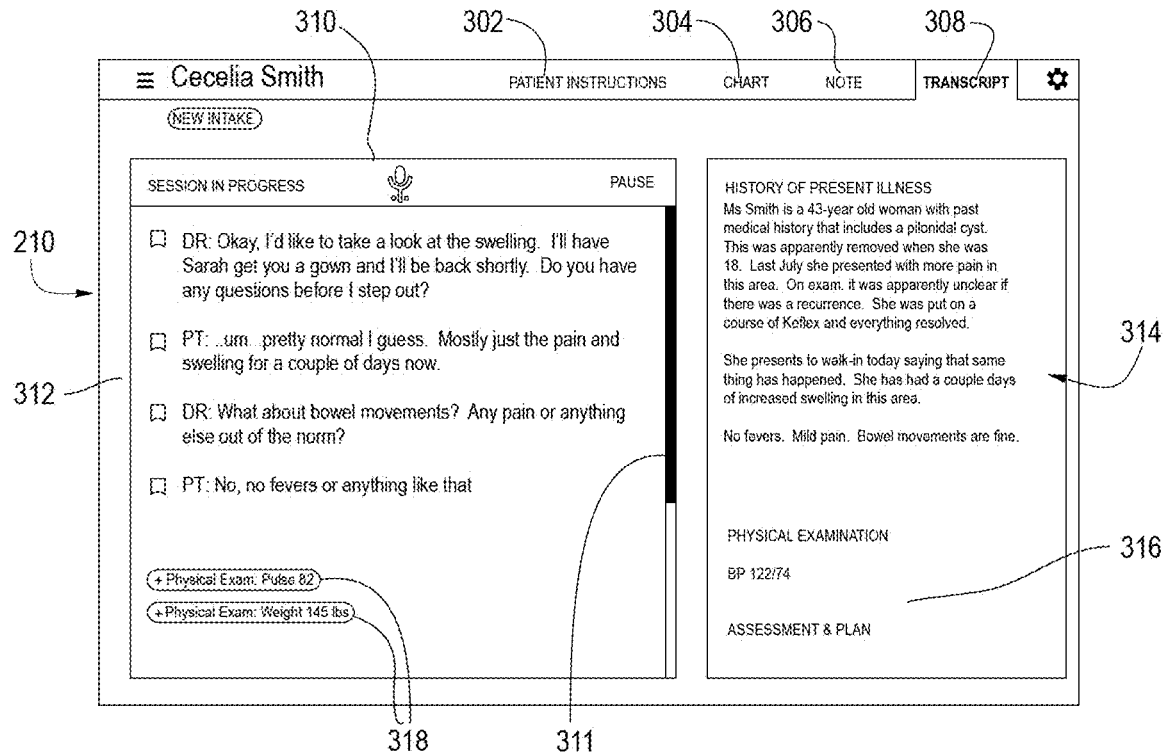
FIG. 3 is an illustration of a transcript and a note generated in substantial real time automatically during the rendering of an audio recording of a patient-healthcare provider conversation.

In FIG. 3, there is shown one possible format of the display of the transcript on the interface of the workstation 210. The page shown includes a transcript tab 308 which has been selected, as well as a note tab 306, a chart tab 304, and patient instructions tab 302. The transcript shown in region 312 is editable, that is the user select highlight words or phrases in the transcript based on the rendered audio recording and edit if they see fit to do so. The speaker icon 310 indicates that the audio recording is being played, and in substantial real time the transcript is generated, line by line. For example, the workstation plays the sound of the patient speaking "No, no fevers or anything like that" and immediately thereafter the transcript is augmented with the new line of text: Pt: No, no fevers or anything like that. The Note region 314 includes a history of present illness, which is generated from data in the electronic health record and/or from speech generated in the visit with the provider. The note includes current physical examination data, such as blood pressure as indicated at 316. The transcript area also includes a listing of current examination data, such as pulse and weight. The pulse and weight data (from recent vital signs in the patient's electronic health record) is generated in response to the highlighted passage at the top of the transcript where the doctor states "I'd like to take a look at the swelling."

It will be appreciated that the note set forth in the note field 314 can be automatically generated from the transcript and making use of the machine learning models of FIG. 1. Validation of the note is possible by matching note segments to the transcript and corresponding audio, e.g., by the linking between highlighted words or phrases in the transcript to the corresponding words or phrases in the note region, and having the audio played at that portion of the transcript. Furthermore, the audio recording tools on the workstation display include pause, rewind, play, fast forward, etc., so that the user can start and stop the recording to listen to sensitive or important patient information and confirm that the transcript, highlighted words or phrases, and insertion of words or phrases into the note are correct.

Figure 4:
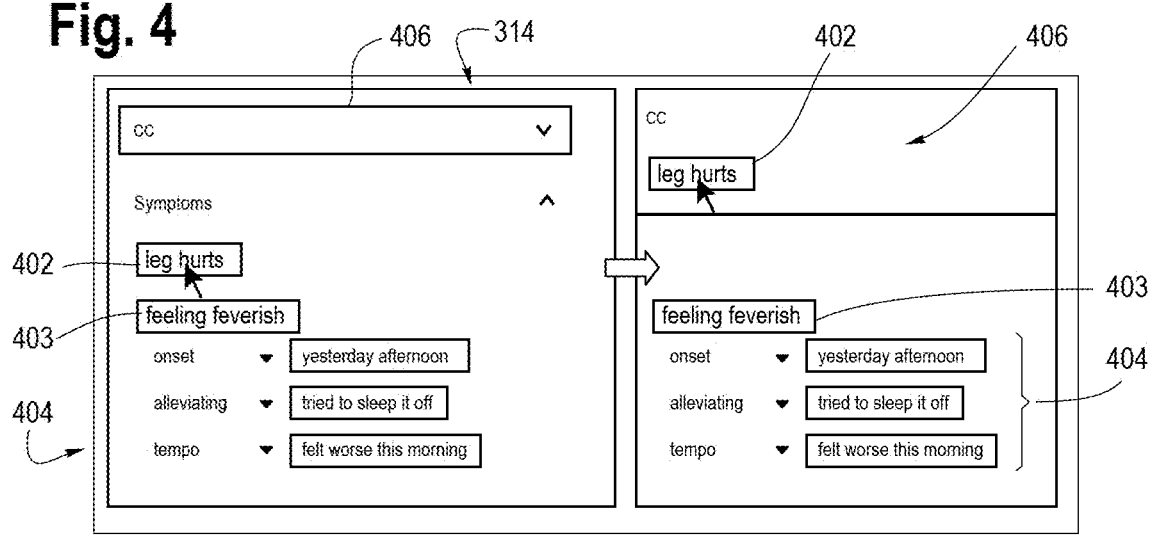
FIG. 4 is an illustration of the ability to edit groupings of highlighted medical events or terms in the note.

FIG. 4 shows an example of how the highlighted phrases "leg hurts", 402, and "feeling feverish" 403 are extracted from the transcript and placed into a note. Furthermore, attributes of the symptom "feeling feverish", and specifically, onset, alleviating, and tempo (404) are also extracted from the transcript and placed into the note. The area 406 is a field for the user to indicate the chief complaint (CC), and whereas originally this field is blank the user is able to click and drag the text "leg hurts" 402 into the CC field 406 as indicated on the right side of FIG. 4. Thus, the grouping of text elements in the note is editable.

Figure 5:
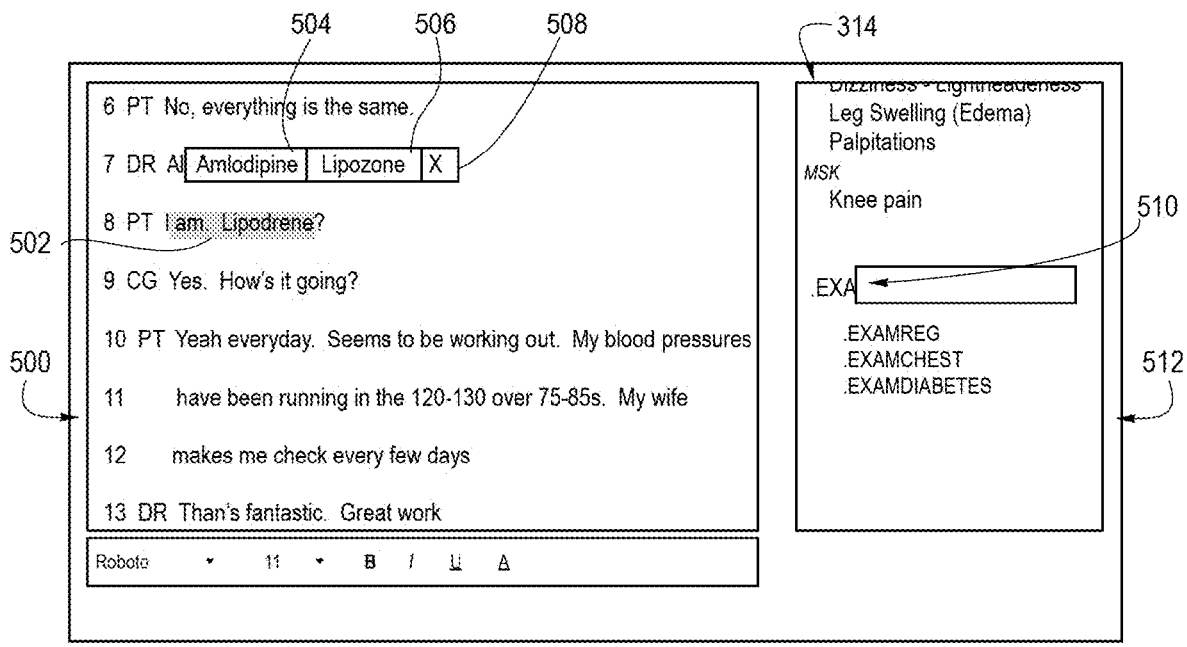
FIG. 5 is an illustration of features for editing the transcript with smart suggestions of words to replace text in the transcript, as well as editing of the note.

FIG. 5 illustrates a further example of editing of a transcript 500 and a note. In FIG. 5, the patient has spoken the phrase "I am. Lipodrene." (502) in response to a question about medication they are taking. The phrase "Lipodrene" is not recognized as a name of a medication and the NER model of FIG. 1 generates two smart suggestions: Amlodipine and Lipozene (504 and 506) which are placed adjacent to the suspect term "Lipodrene." The user can accept either of these suggestions by clicking on them, or reject them by activating the X icon 508. In the note region 314 there is a note 512 being generated automatically as the transcript is created. The user has typed in the term .EXA (510) to search for an examination entry into the note and suggested completions of the .EXA search are shown based on the search query. The note is editable to move classifiers and groupings or to add new content. When entering new content, the doctor can use the equivalent quick keys ("smart phrases" or "dot phrases") of the facility's Electronic Health Record system, such as shown in this example with the .EXA search.

Figure 6:
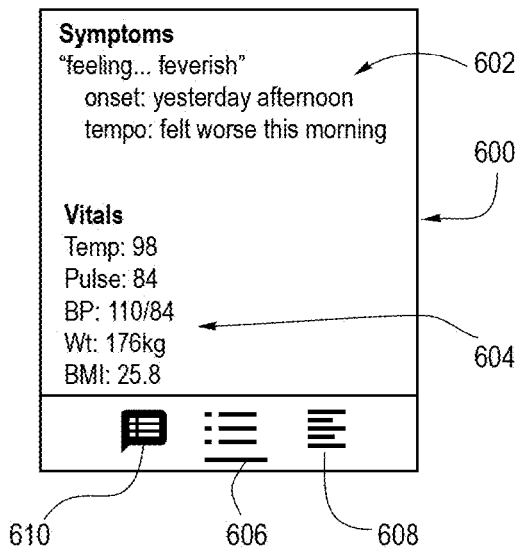
FIG. 6 shows an example of a note being generated in substantial real time in a bulleted list format, and tools at the bottom of the display to switch the note presentation between a bulleted list and prose style.

FIG. 6 shows a note being generated automatically as the transcript of a conversation is generated, in which the note 600 is in the form a bulleted list. In this particular example, there is a bullet item "Symptoms" and under this heading there is the phrase "feeling . . . feverish" 602 (a quotation from the transcript) along with additional attributes of the symptom, namely onset and tempo. The note 600 further includes vital signs 604. There are icons at the bottom of the note to trigger additional forms for the display of the note, namely icon 610 which triggers display of the transcript side by side with the note, icon 606 which triggers the display of the bulleted list as shown in FIG. 6, and icon 608 which triggers display of the note in a prose style.

Figure 7:
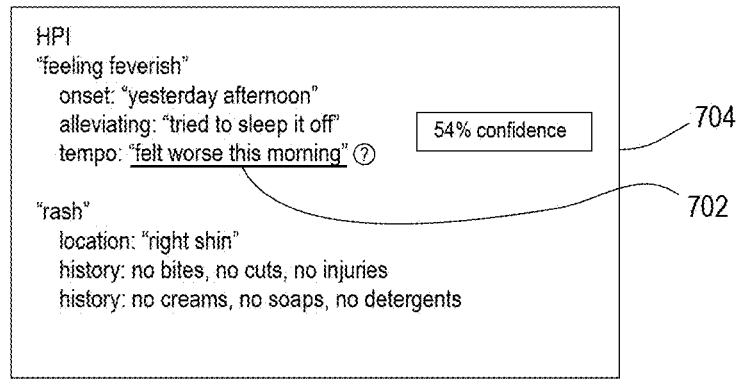
FIG. 7 is an illustration of a confidence indicator for a phrase appearing in the note.

FIG. 7 shows an example of a display of a confidence indicator 704 which is generated when there is uncertainty in either the speech that was recorded or in suggestions that are generated by the machine learning models. For example, the spoken phrase "felt worse this morning" (702) may have been muffled or poorly recorded and the speech to text converter model may have only a 54 percent confidence that this is what the patient spoke. The user can click on the phrase "felt worse this morning" at which point the transcript is displayed at that location and the audio phrase is replayed. The user can accept or reject (i.e., edit) the note. The confidence indicator could also be displayed for suggestions, such as the suggestions shown in FIG. 5 for the spoken word "Lipodrene." Suggested words or phrases that have high confidence levels (e.g. >80%) will ordinarily not be accompanied by confidence indicators, and words or phrases that have a low confidence level, e.g., <30%, would ordinarily not be suggested to the user. Thus, the confidence levels are only provided for suggested words and phrases with intermediate levels of confidence, say between 30 and 80 percent or between 30 and 70 percent.

Figure 8:
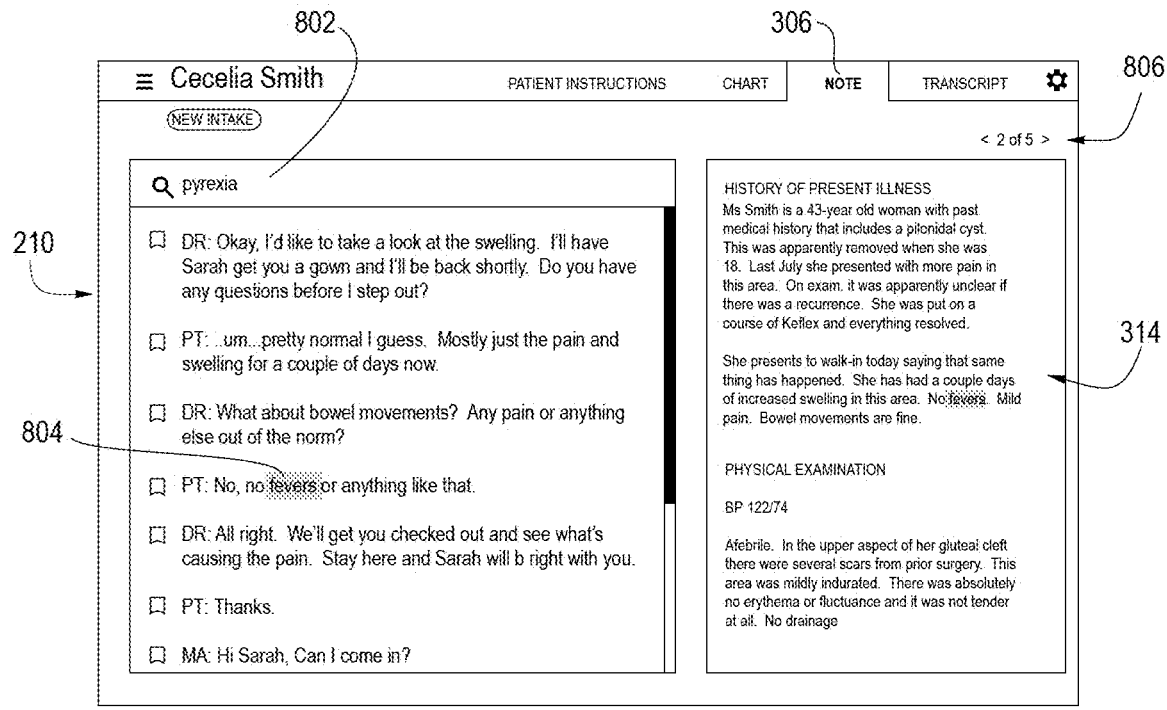
FIG. 8 is an illustration of a smart searching tool for searching across a transcript and a note.

FIG. 8 shows an illustration of the workstation 210 when the user has selected the Note tab 306. The transcript is displayed along with the note in region 314, in this example in prose style. The page includes a search tool 802 in which the user is searching for the term "pyrexia" in either the transcript or the note. The search function is a "smart" search function, meaning that equivalents to "pyrexia" (i.e., fever, feverish, hot, sweaty etc.) in the transcript are also found. In this case, the transcript has five hits (see region 806) and the transcript is showing the second hit, namely the patient mentioning of fever at 804. Additionally the term "fever" in the note region 314 is highlighted.

Figure 9:
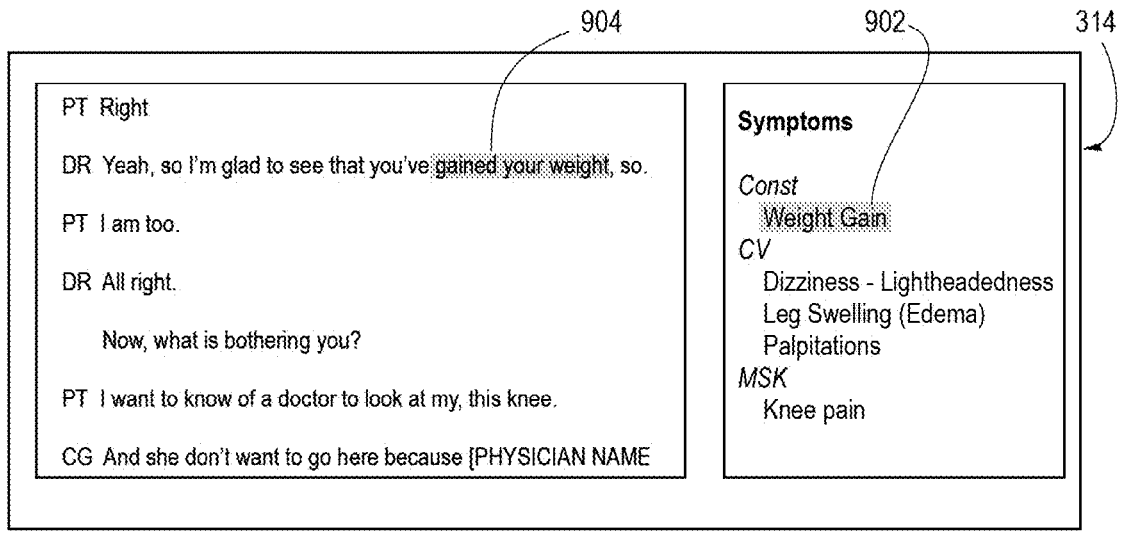
FIG. 9 is an illustration of a linking or mapping between note segments and words in the transcript and corresponding audio portion.

FIG. 9 is an illustration of how selecting a note segment maps or translates to the corresponding portion of the transcript and the audio recording. In this example, the user has clicked on the phrase "weight gain" 902 in the note region 314, and the corresponding portion of the transcript that is linked to the note phrase "weight gain" is shown highlighted on the same screen. In this example, the Doctor mentioned that "gained your weight" as indicated at 904. Similarly, if the user were to select "knee pain" under the MSK category under the Symptoms bullet, the relevant portion of the transcript where the patient spoke a complaint about knee pain would be shown with the phrase "pain in my knee" in the transcript highlighted. The user has the option to play the audio recording at the lines containing the highlighted words to verify accuracy of the speech to text conversion.

Figure 10:
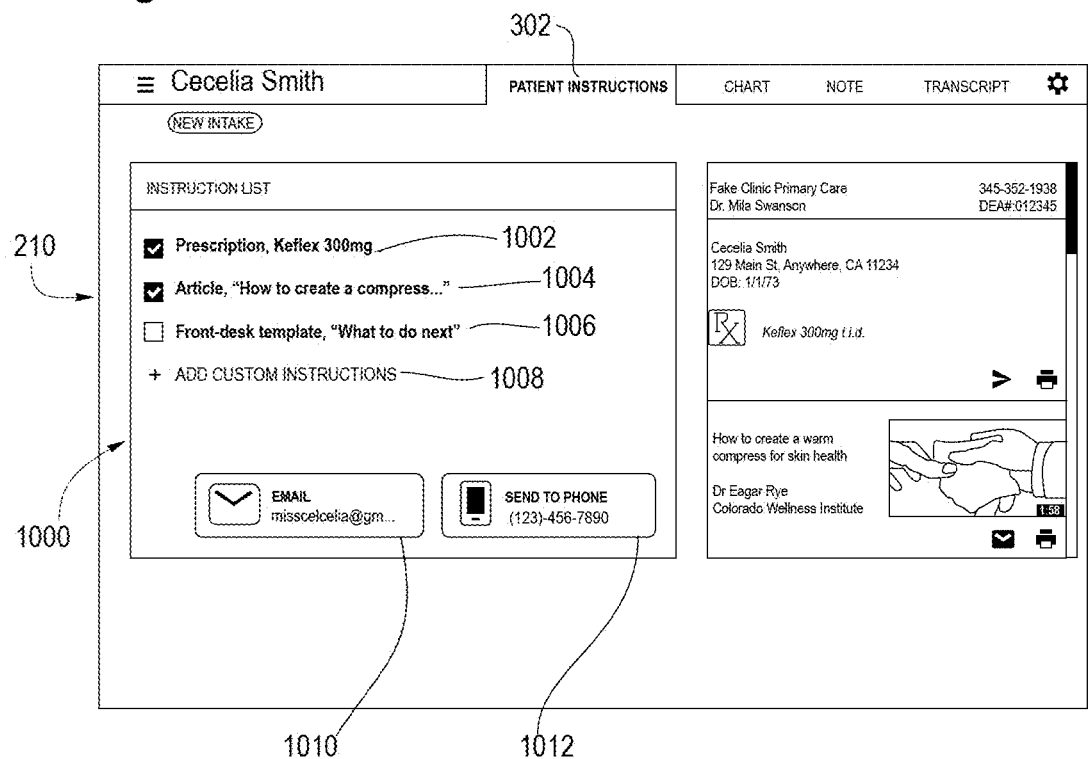
FIG. 10 is an illustration of a patient instructions screen in which all patient instructions are gathered in one spot, and providing tools for managing a checklist of patient instructions, including adding or removing handouts for the patient.

FIG. 10 is an illustration of the workstation 210 display where the user has selected the patient instructions tab 302. In this display there is a region 1000 were all patient instructions are gathered in one location for easy viewing and transmitting to the patient. In this example, the patient instructions include a prescription (1002), an article to read (1004) and an option to select a template "what to do next" (1006). A check box is next to the prescript and article fields 1002 and 1004 which can be unchecked in case the users wishes to cancel these particular instructions. By checking the open check box next to the template description 1006 this template would be added to the instructions. There is a field 1008 for the user to add custom instructions. When this field 1008 is selected there is a pop-up window with a list of handouts or instructions which are available for selection to send to the patient. At the bottom of the page there is an icon 1010 to send all the instructions to the patient via email. If icon 1012 is selected the instructions are sent by SMS message to a smart phone or tablet of the patient. Further details on any of the templates, articles or other custom instructions can be displayed on the right hand side of the page of FIG. 10. A scroll bar is included to scroll down through all the detailed information on the instructions since they may not all be presented on the display at one time.

Figure 11:
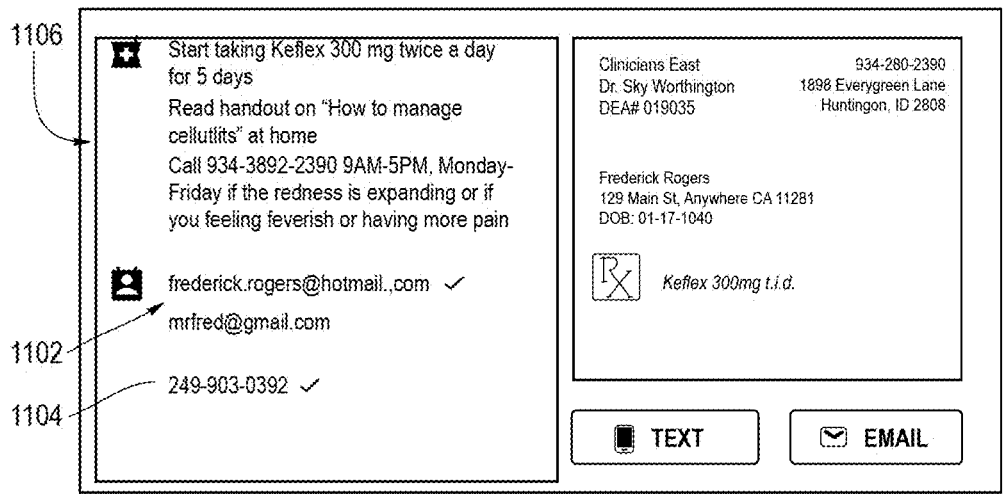
FIG. 11 is an illustration of set of patient instructions along with options to change SMS or email preferences for contacting the patient.

FIG. 11 shows another version of a further display 1106 of instructions for the patient, as well as a field for showing contact information for the patient, including email addresses 1102 and phone number(s) 1104. This page presents the option to change SMS or email preferences among the list of contact information shown at 1102 and 1104 by either selecting or unselecting them with the mouse.

Figure 12:
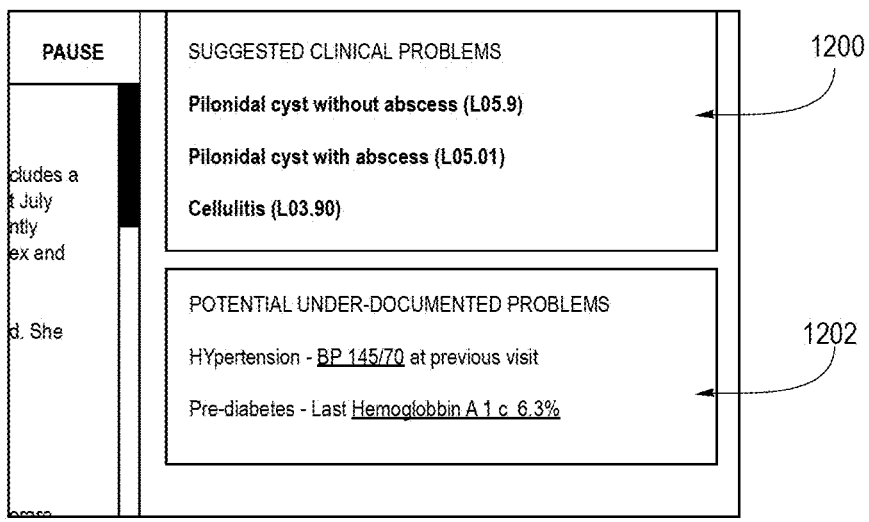
FIG. 12 is a display of a suggested problem list that supports physicians in their decision making which can be generated in substantial real time during the rendering of the recording of the conversation with the patient. Potential problems that need addressing but that have not been brought up by the patient are also flagged.

FIG. 12 shows an additional feature of the machine learning models which are used in extracting highlighted text in the transcript. The machine learning models are trained from labeled training data such that as patients discuss their issues or symptoms, a suggested problem list is generated and displayed on the workstation to support doctors in decision making. Clinical decision support models generating suggested problem lists or questions for physicians are known in the art therefore a description is omitted for sake of brevity. For example, the patient-doctor conversation may result in the generation of suggested clinical problems shown at 1200 in FIG. 12, including diagnostic billing codes. Additionally, problems that need addressing but that have not been brought up by the patient in the conversation may also be flagged. This is shown in the list of potential under-documented problems as indicated at 1202 in FIG. 12. In this example, hypertension is flagged because at the previous visit the patient was showing high blood pressure readings. Pre-diabetes is also flagged because the last hemoglobin ATc measurement of 6.3% indicated that the patient has the potential for becoming diabetic. The display of these suggested clinical problems and under-documented problems can be generated on the workstation in the clinic or physician office during the patient visit, in substantial real time, therefore the healthcare provider can address these issues with the patient during the office visit then and there.

Figure 13:
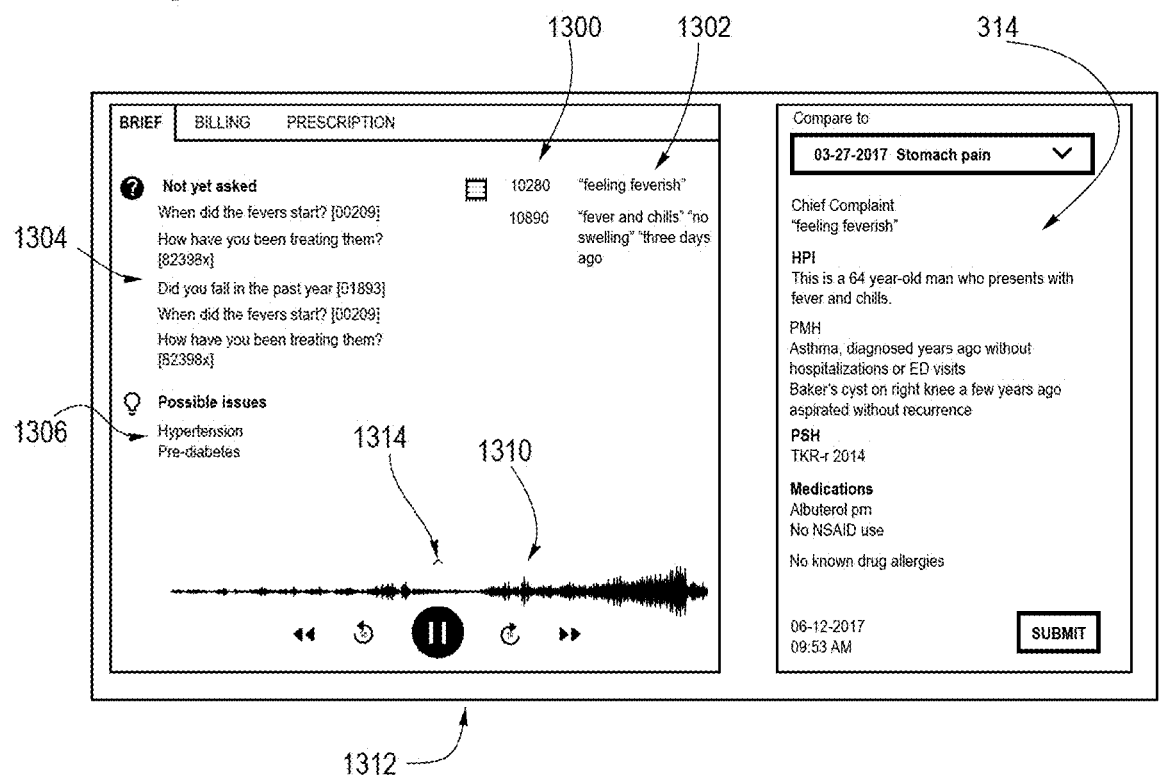
FIG. 13 is a further list of questions that are presented to the physician which have not been asked, as well as suggested alternative diagnoses and billing codes.

FIG. 13 illustrates a page displayed on the workstation of FIG. 2 when the user has toggled to a Billing tab. The page includes a display of billing codes 1300 and corresponding text 1302 from the note supporting the billing codes. The region 1304 displays a list of pertinent questions which are not yet asked, such as "when did the fever start" along with a reference to the line of the transcript (line 209) where the patient mentioned that they felt feverish. The page also displays possible issues to explore with the patient, such as hypertension and pre-diabetes. The bottom of the page shows a region 1312 indicating the audio recording is available for play, along with tools 1310 to pause, play, fast forward, rewind, etc. the recording. The transcript of the conversation is displayed when the up-arrow icon (A) 1314 is activated. In this example, the note in region 314 is displayed in a prose style.

Figure 14:
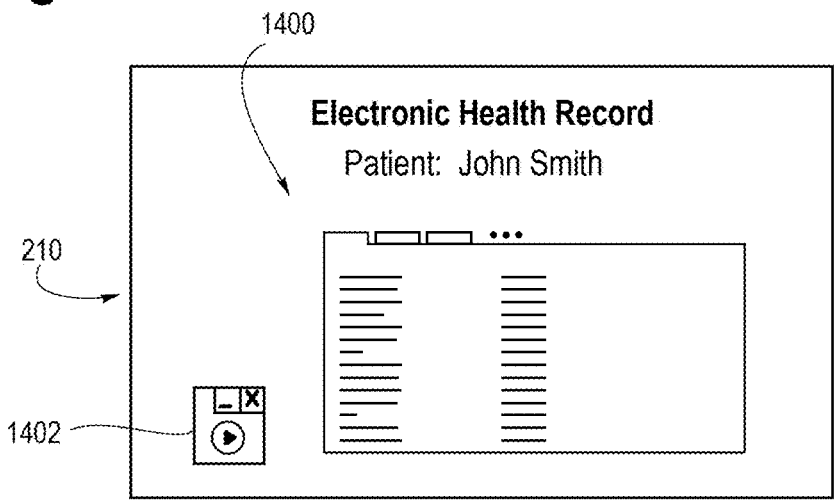
FIG. 14 is an illustration of a minimized widget (icon) on the main display of the terminal of FIG. 2, which allow for access to the transcript and recording of the visit but which also allows the physician to navigate through other patient data.

FIG. 14 illustrates a feature by which smart scaling is included in the display on the workstation to allow access to the audio recording and the transcript and at the same time navigating to other patient data. In this example, the workstation shows the electronic health record of a patient, including a multitude of tabs for showing various component parts of the record (medications, family history, vital signs, prior procedures, prior notes, etc.). There is also shown a small icon 1402 at the periphery of the display for playing or pausing the recording. For example, if the user was listing to the recording and viewing the transcript but wanted to explore other aspects of the patients records, they could minimize the display (e.g., the display of FIG. 3, or FIG. 13) and navigate to the patient's entire electronic health record and explore what data there may be in there of interest to the current discussion in the patient-provider conversation. Meanwhile, while the user is navigating through the electronic health record, the small icon 1402 remains on the page. By selecting it they can resume the rendering of the audio recording and the simultaneous generation of the transcript and the note as explained above. This interface, e.g., of FIG. 3-12 can be minimized during the visit and still actively record the patient visit, to allow the doctor access to other desktop tools.

Once the healthcare provider has completed the process of reviewing and editing the transcript and note it can be downloaded and stored locally, e.g., in the electronic health record for the patient in the data store 212 shown in FIG. 2 or on the hard drive of the workstation 210.

In view of the above, it will be appreciated that we also described a system for facilitating automatic generating a note summarizing a conversation between a patient and a healthcare provider. The system includes a workstation 210 having a tool (icon, link or other) for rendering an audio recording of the conversation and generating a transcript of the audio recording using a speech-to-text engine, e.g., as shown in FIG. 3. The workstation includes a display (FIG. 3) having a first transcript region (312, FIG. 3) for display of the transcript of the recording and simultaneously a second note region (314, FIG. 3, FIG. 4, FIG. 13, etc) for display of a note summarizing the conversation. A trained machine learning model (FIG. 1, 104) extracts words or phrases in the transcript related to medical topics relating to the patient, and in the system the extracted words or phrases are displayed in the note region 314 of the display (FIG. 4, FIG. 17, etc.). The extracted words or phrases in the note region 314 are linked or mapped to the portions of the transcript from which the extracted words or phrases originated whereby the source and accuracy of the extracted words or phrases can be verified by a user of the workstation, e.g., as explained above in conjunction with FIG. 3, 4 etc.

Further by way of summary, the system and method of this disclosure features a number of possible and optional variations or enhancements, such as: the extracted words or phrases are placed into appropriate categories or classifications in the note region such as symptoms, medications, etc., as shown in FIG. 6, 7, 9, 17, 18, etc. Additionally, the speakers are identified in the transcript, e.g., FIGS. 3, 8 and 19. The transcript and note are editable, e.g., as shown in FIG. 5. The method may further include the step of automatically generating suggestions of alternative words or phrases for words or phrases in the transcript and tools to approve, reject or provide feedback on the generated suggestions to thereby edit the transcript, e.g., as described in FIG. 5 above. The method and system may rendering the note in a prose style, e.g., as shown in FIG. 8, or in the form of a bullet list, e.g., FIGS. 6, 17, 18. Words or phrases in the transcript relating to symptoms or attributes of such symptoms are grouped and classified together within the note, e.g., as shown in FIGS. 7, 9, 17, 18. The note is editable to change classifications and groupings of symptoms and symptom attributes, e.g., as shown in FIG. 4. The method and system may also provide for displaying a confidence level for generated suggestions of alternative words or phrases, e.g., as shown in FIG. 5. As shown in FIGS. 12 and 13, there may be a display of at least one of suggestions of topics to follow-up with the patient, suggestions of clinical problems, suggestions of potential under-documented problems, and suggested billing codes with portions of the transcript displayed which justify the billing codes. Additionally, there may be a step of displaying an emailable or SMS-ready list of patient instructions (FIGS. 10 and 11), including features for editing the list of instructions, adding new instructions from a list of available or suggested instructions, medication changes, or additions from a list generated from the assessment and plan portion of the doctor's notes. As shown in FIG. 14, the method may further include displaying a minimized icon (1402) on a display of an electronic health record screen which, when activated, toggles to the audio recording of the conversation and the transcript thereof.

Additional possible features include displaying on the workstation display a search tool to search for words or phrases to insert into the note, e.g., as shown in FIGS. 5 and 8. FIG. 8 shows a smart search tool permitting searching across the transcript and note for words or phrases identical to and equivalent to a word or phrase entered into the smart search tool. The search tool of FIG. 5 integrates smart phrase or dot phrase search shortcuts present in the electronic health record of the patient.

B. Automated Generation of Transcripts of Patient-Healthcare Provider Conversations and Visual Indicators to Build Confidence and Trust in the Transcript This disclosure also relates to a method for generating a transcript of an audio recording of a patient-healthcare provider conversation. The disclosure is related to methods to increase the trust in the transcript and the credibility and confidence in the behind the scenes processing to create the transcript. As noted previously, physicians spend 20-30 percent of their time on average documenting patient visit notes for proper billing. Capturing audio during a patient's examination and generating an automatic transcript, rather than relying on manual or computer note-taking, allows doctors to focus on their patients and expedites a doctor's ability to write notes. Technology that extracts relevant medical concepts from the transcript can streamline documentation writing even more. However, the medical decision making process is incredibly complex. Before integrating the outputs of machine intelligence into their practice's workflows, doctors must feel like they understand how and why these automatic recommendations are made.

At the same time, doctors are already overloaded with information. The present disclosure provides transparency into the machine transcription and information extraction process to build trust and credibility, while also at the same time minimizes the impact on the user's attention. To accomplish this, we developed novel user interfaces and interactions that provide supportive emphasis and rapid understanding of machine intelligence outputs.

As will be explained below, transcripts are annotated (i.e., highlighted) with contextual information to promote trustworthiness and credibility. Audio during patient/clinician interactions is captured and transcribed in substantial real-time, with words appearing on a user interface of a workstation shortly after being spoken. The doctor can confirm at any time that audio is being recorded accurately.

Also in real-time, phrases for use in the medical note are auto-extracted from the transcript. Selecting a suggested note extract toggles to the corresponding part of the transcript. These note highlights are appended with suggested groupings per symptom and classifiers per billing codes (tempo, onset, etc.) all of which can be approved or rejected by the doctor.

The method uses a workstation (210, FIG. 2, 3) which provides for a rendering of an audio recording of the conversation (e.g., through a speaker on the workstation) and generating a display of a transcript of the audio recording (FIG. 3) using a speech-to-text engine in substantial real time with the rendering of the audio recording. The generating of the transcript in substantial real time with the rendering of the audio recording enables inspection of the accuracy of conversion of speech to text. The workstation includes a tool such as a scroll bar for scrolling through full length of the transcript and rendering the portion of the audio according to the position of the scrolling. Thus, the user can navigate through the transcript and re-play the portion of the audio at particular points in the transcript to confirm the accuracy of the conversion of speech to text.

Additionally, the method involves highlighting in the transcript words or phrases spoken by the patient relating to symptoms, medications or other medically relevant concepts relating to the medical condition of the patient. For example if the patient says "I felt feverish this morning" the phrase "felt feverish" or just "feverish" and the phrase "this morning" would be highlighted in the transcript, as they are relating to symptoms and onset of symptoms experienced by the patient. This feature calls out to the user's attention particularly important or significant words or phrases in the transcript.

Additionally, the method provides a set of transcript supplement tools which enable editing of specific portions of the transcript based on the content of the corresponding portion of audio recording. In particular, there may be portions of the audio recording where the patient's voice may be muffled, they may mispronounce a significant word, such as the name of a medication, they only remember the first syllable or the pill color of the medication they are taking, etc. The transcription supplement tools enable editing of these portions of the transcript, such as by displaying suggested alternative phrases, displaying corrected medical terminology, displaying suggestions for incomplete words, etc., and tools for accepting, rejecting or editing the transcript and the generated suggestions. Additionally, these suggestions may be accompanied by a display of an indication of confidence level in auto-suggested words or phrases.

The method of generating the transcript may be accompanied by other optional features, such as displaying a note simultaneously with the display of the transcript and populating the note with the highlighted words or phrases, e.g., as shown in FIG. 9. Additionally, the transcript may be minimized and the workstation may provide for viewing the note only, which is generated in substantial real time with the rendering of the audio recording. Additionally, the highlighted words or phrase are placed into appropriate categories/classifications in the note such as symptoms, medications, etc. Supplementary information may be provided for symptoms including labels for phrases required for billing. There is also a linking of elements in the note to relevant parts of the transcript, for example if the user clicks on a the phrase "felt feverish" under a symptom heading in the note the relevant portion of the transcript where the patient describe this symptom is displayed adjacent to that portion of the note.

The following sections will describe further aspects of the method of generating the transcript or use thereof which builds trust in the transcript and credibility of the processing behind the scenes.

A. Real-Time Transcript that Scrolls/Updates

Figure 15:
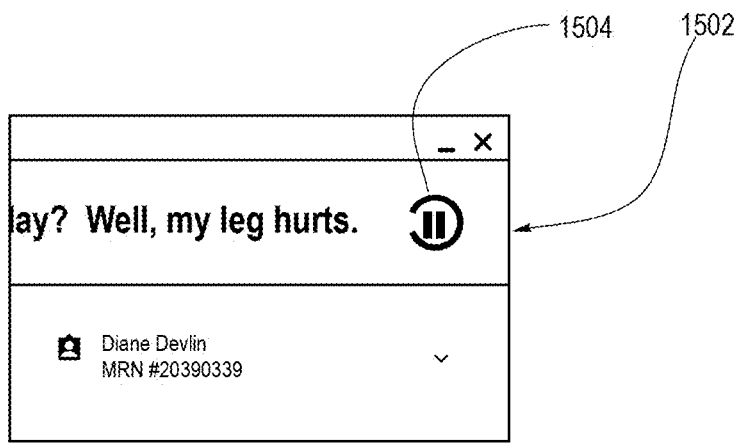
FIG. 15 is an illustration of a generation of a transcript in substantial real time with the rendering of the audio recording, allowing the physician to view the transcript for accuracy.

As shown in FIG. 3, as the patient and clinician are talking (or later on when the audio recording is rendered on the workstation) there is an automated generation of a transcript in real time that scrolls and updates additional speech is recorded. FIG. 15 shows another example of this. There is a display 1502 on the workstation including audio controls 1504 (such as play, pause, fast forward etc.) that control the rendering of the audio recording and as it plays the sound of the patient speaking "well, my leg hurts" there is display of a transcript of the speech ("well, my leg hurts). This display as shown in FIGS. 3 and 15 provides a visual indication that the speech phrases are being captured and transcribed accurately.

B. Highlights in the Transcript

Medically relevant words or phrases in the transcript are called out or highlighted. For example, in FIG. 16 the patient has spoken the phrase "Well, my leg hurts" and the phrase "leg hurts" is shown in bold. Two lines later the patient states that they started to feel feverish and the words "feeling" and "feverish" are also highlighted. The manner of highlighting is not particularly important and could take many forms, such as use of red font, larger font, bold face, underlining, etc. Again, as the audio recording is rendered and the transcription generated these medically relevant words or phrases are highlighted immediately as the transcript is produced.

C. Minimize Transcript and Toggle to the Note-Only View

Figure 16:
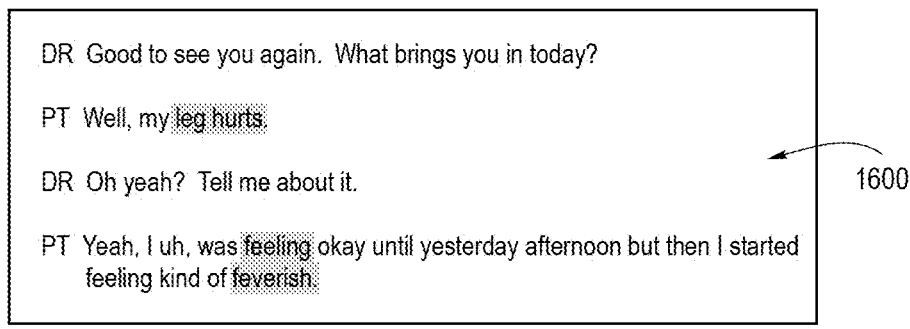
FIG. 16 is another form of the transcript which is generated line by line as the recording of the patient-healthcare provider conversation is played on the workstation.

As the recording is rendered and the transcript generated as shown in FIGS. 3, 15 and 16, the physician may want to focus on the note generation process instead of the transcript per se and so the display includes a minimization tool for minimizing the region of the display where the transcript is produced and thereby toggle to a note-only view. For example, in FIG. 17 there is shown a display of the words or phrases forming a note in the note region 314 under appropriate headings or categories, in this case a symptom category. FIG. 17 is like the illustration in FIG. 6, however, in FIG. 17 the patient has just spoken the phrase "I developed a rash on my right shin" and immediately the words "rash" (1702) and "right shin" (1704) are then placed in the note under the symptom heading.

D. Note Suggesting Grouping/Classifiers

As the word or phrase excerpts from the transcript are placed into the note they are grouped into recommended sections, aligned with how notes are currently structured in practice. Supplementary information for symptoms include labels of key phrases required for billing, as suggested by the machine learning models of FIG. 1. For example, in FIG. 18, there is shown a note region 314 in which the phrase "leg hurts" is placed in a section entitled "chief complaint". Under the history of present illness section (HPI) there is a list of additional symptoms extracted from the transcript including onset, alleviating and tempo.

E. Ability to Accept/Reject Transcript and Note Suggestions

The user interface shown in the Figures includes the ability to edit the transcript and the note, including the ability accept or reject suggestions for the transcript and note, e.g., when the words are misspoken, the speech is muffled or partially inaudible, or other situations arise when the speech recognition engine is not confident as to the words spoken. In the example of FIG. 19 the patient was asked about the medication and state the name "Lipodrene", a term not in the vocabulary of the NER model, and the user is presented with two alternatives 1904 and 1906 which may the name of the medication the patient intended to say. The user can select either one or reject them by activating the X icon 1908. Furthermore, the user can change classifications for the suggestions, through moving items to different groupings, changing drop downs, deleting suggestions or adding more context. An example of this was shown in FIG. 4 with the moving of the moving of the extracted phrase "leg hurts" from the symptoms region in the note to the chief complaint region of the note.

F. Transcript Suggestion for Uncertain Phrases

Figure 20:
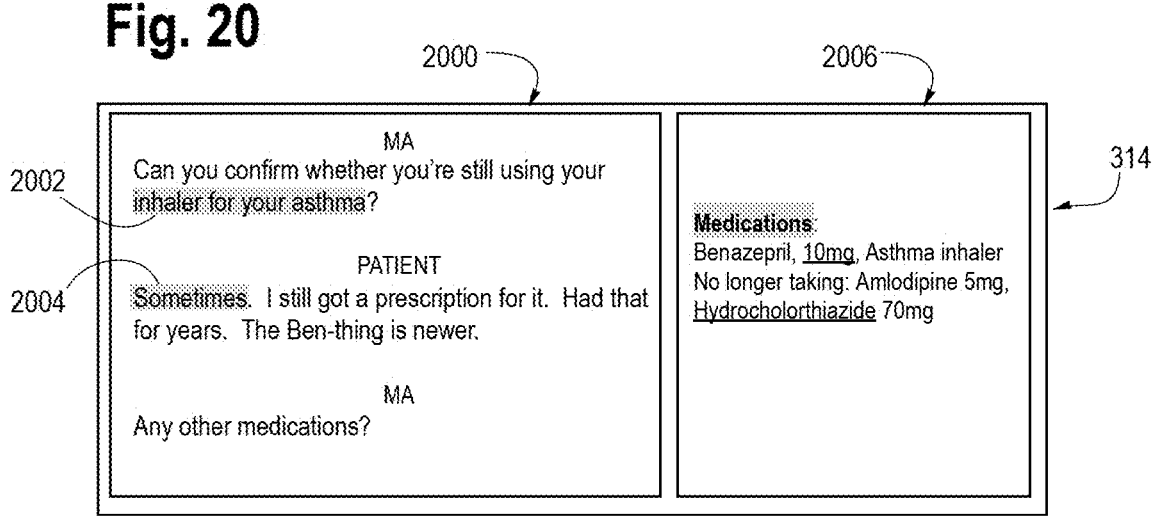
FIG. 20 is an illustration of display of transcript suggestions for uncertain phrases.

If the automated speech recognition function in the speech to text converter model (FIG. 1) is unable to pick up a phrase, or perhaps patients are unsure of the right word (especially in regards to medication names) the interface provides for automatically suggesting appropriate alternative words or phrases. In FIG. 20, there is shown a portion of a transcript 2000 in which the physician ("MA") asked the patient if they were still using their inhaler for their asthma (2002) with "inhaler for your asthma" highlighted. The patient then mentions "Sometimes", which is highlighted, and then a few sentences later says "The Ben-thing is newer." The word "Ben-thing" is not recognized and so the NER model proposes the display of the medication Benazepril, 10 mg, asthma inhaler in the note region 314. The user can accept, edit or reject the suggestion of including Benazepril 10 mg in the note.

G. Transcript Confidence Indicator for Muffled Phrases

As was described previously in conjunction with FIG. 7, for phrases that are auto-suggested the display includes an expectation of the certainty about the suggestion. This display of confidence levels may also apply to display of terms in the note and not just terms in the transcript.

H. Link Note to Relevant Parts of the Transcript

As explained previously, there is a linking or mapping between the note fragments (words or phrases) and the portions of the transcript from which such fragments originated. Thus, the note fragments can be clicked or tapped to view how they were generated based on what was stated through the transcript. See the previous discussion of FIG. 9.

I. Terminology is Adapted to Professionally Preferred Terms

Figure 21:
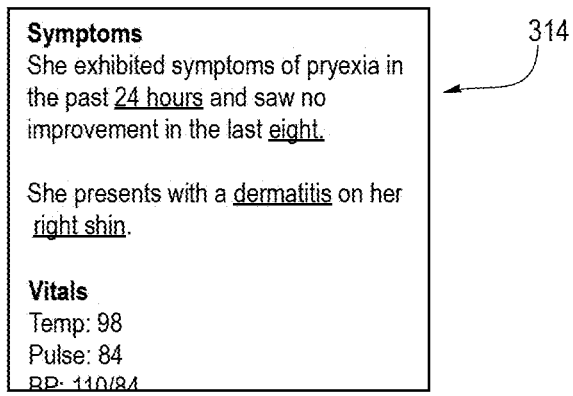
FIG. 21 is an illustration of a prose-style note with terminology adapted to professionally preferred terms.

In applicable cases the terminology in the note is adapted to professionally preferred terms. For example, in FIG. 21 the note has replaced "rash" with "dermatitis" and "feeling feverish" with "pyrexia."

In view of the above, we have described a workstation (210) displaying a transcript of a conversation between a patient and a healthcare provider. The workstation includes a tool, e.g., icon, tab, link, etc. for a rendering of an audio recording of the conversation and generating a display of the transcript of the audio recording using a speech-to-text engine in substantial real time with the rendering of the audio recording, thereby enabling inspection of the accuracy of conversion of speech to text. See e.g., FIGS. 3, 15, 16. The workstation further includes a tool such as scroll bar (311, FIG. 3) for scrolling through the full length of the transcript and rendering the portion of the audio according to the position of the scrolling. The display of the transcript including a highlighting of words or phrases spoken by the patient relating to symptoms, medications or other medically relevant concepts, see FIGS. 3, 8, 9 etc. The workstation further includes a set of transcript supplement tools enabling editing of specific portions of the transcript based on the content of the corresponding portion of audio recording.

What is claimed is:

1. A method for generating a transcript of a conversation between a patient and a healthcare practitioner, comprising:
    providing a rendering of an audio recording of the conversation and generating a display of the transcript of the audio recording using a speech-to-text engine in substantial real time with the rendering of the audio recording;
    enabling scrolling through the transcript and rendering a portion of the audio recording according to a position of the scrolling;
    automatically recognizing, in the transcript or in the audio recording, words or phrases spoken by the patient relating to one or more of symptoms, medications or other medically relevant concepts; and
    displaying a note simultaneously with the display of the transcript and populating the note with the words or phrases in substantial real time with the rendering of the audio recording.

2. The method of claim 1, further comprising:
    providing a set of note supplement tools enabling editing of specific portions of the note based on a content of a corresponding portion of the transcript or the audio recording.

3. The method of claim 2, wherein the set of note supplement tools include at least one of:
    a) a display of smart suggestions for words or phrases and a tool for editing, approving, rejecting or providing feedback on the smart suggestions;
    b) a display of suggested corrected medical terminology; and
    c) a display of an indication of confidence level in suggested words or phrases.

4. The method of claim 3, wherein the set of note supplement tools include each of the displays a), b) and c) recited in claim 3.

5. The method of claim 3, wherein the display of the indication of the confidence level comprises display upon a determination that the confidence level exceeds a threshold confidence level.

6. The method of claim 1, further comprising:
    minimizing display of the transcript and viewing the note only, and wherein the note is generated in substantial real time with the rendering of the audio recording.

7. The method of claim 1, wherein the words or phrase are placed into appropriate categories or classifications in the note.

8. The method of claim 1, further comprising:
    providing, in the note, supplementary information for symptoms including labels for phrases required for billing.

9. The method of claim 1, further comprising:
    a set of transcript supplement tools to enable editing of specific portions of the transcript based on a content of a corresponding portion of the audio recording.

10. The method of claim 1, further comprising:
    linking words or phrases in the note to relevant parts of the transcript from which the words or phrases in the note originated.

11. The method of claim 1, wherein the automatically recognizing of the words or phrases is performed by using a trained machine learning model.

12. A server for displaying a transcript of a conversation between a patient and a healthcare practitioner, comprising:
    one or more processors; and
    memory storing computer-executable instructions that, when executed by the one or more processors, cause the server to:
        receive an audio recording of the conversation;
        apply a machine learning model to generate the transcript of the audio recording using a speech-to-text engine in substantial real time with a rendering of the audio recording, wherein the machine learning model is trained to automatically recognize, in the audio recording or in the transcript, words or phrases spoken by the patient relating to one or more of symptoms, medications or other medically relevant concepts; and
        transmit the transcript by an application programming interface to a workstation, and wherein the instructions cause the workstation to:
            generate a display of the transcript of the audio recording;
            provide a user interface element enabling scrolling through the transcript and rendering a portion of the audio according to a position the scrolling;
            automatically recognize, in the transcript, words or phrases spoken by the patient relating to one or more of symptoms, medications or other medically relevant concepts; and
            display a note simultaneously with the display of the transcript and populating the note with the words or phrases in substantial real time with the rendering of the audio recording.

13. The server of claim 12, wherein the instructions cause the server to:
    apply the machine learning model to generate the note in substantial real time with the rendering of the audio recording; and
    transmit the note by the application programming interface to the workstation.

14. The server of claim 12, wherein the instructions further cause the workstation to:
    provide a set of note supplement tools enabling editing of specific portions of the note based on a content of a corresponding portion of the transcript or the audio recording.

15. The server of claim 14, wherein the set of note supplement tools include at least one of:
    a) a display of smart suggestions for words or phrases and a tool for editing, approving, rejecting or providing feedback on the smart suggestions;
    b) a display of suggested corrected medical terminology; and
    c) a display of an indication of confidence level in suggested words or phrases.

16. The server of claim 15, wherein the display of the indication of the confidence level comprises display upon a determination that the confidence level exceeds a threshold confidence level.

17. The server of claim 12, wherein the instructions further cause the workstation to:
provide, in the note, supplementary information for symptoms including labels for phrases required for billing.

18. The server of claim 12, wherein the instructions further cause the workstation to:
link words or phrases in the note to relevant parts of the transcript from which the words or phrases in the note originated.

19. The server of claim 12, wherein the instructions further cause the workstation to:
minimize display of the transcript and enable viewing of the note only.

20. An article manufacture comprising one or more computer readable media having computer-readable instructions stored thereon that, when executed by one or more processors of a computing device, cause the computing device to:
provide a rendering of an audio recording of a conversation between a patient and a healthcare practitioner, and generate a display of a transcript of the audio recording using a speech-to-text engine in substantial real time with the rendering of the audio recording;
enable scrolling through the transcript and render a portion of the audio recording according to a position of the scrolling;
automatically recognize, in the transcript or in the audio recording, words or phrases spoken by the patient relating to one or more of symptoms, medications or other medically relevant concepts; and
display a note simultaneously with the display of the transcript and populate the note with the words or phrases in substantial real time with the rendering of the audio recording.

* * * * *